United States Patent
Ikeda

(10) Patent No.: US 6,912,887 B2
(45) Date of Patent: Jul. 5, 2005

(54) OXYGEN SENSOR ABNORMALITY DETECTING DEVICE HAVING OFFSET VOLTAGE CIRCUIT

(75) Inventor: Toshiaki Ikeda, Chiryu (JP)

(73) Assignee: Denso Corporation, Kariya (JP)

( * ) Notice: Subject to any disclaimer, the term of this patent is extended or adjusted under 35 U.S.C. 154(b) by 61 days.

(21) Appl. No.: 10/669,506

(22) Filed: Sep. 25, 2003

(65) Prior Publication Data

US 2004/0100271 A1 May 27, 2004

(30) Foreign Application Priority Data

Oct. 7, 2002 (JP) ........................................ 2002-293738

(51) Int. Cl.⁷ .............................................. G01R 31/08
(52) U.S. Cl. ...................................... 73/1.06; 324/523
(58) Field of Search .............................. 73/1.06, 1.07; 324/512, 522, 523, 524

(56) References Cited

U.S. PATENT DOCUMENTS

| | | | |
|---|---|---|---|
| 4,337,745 A | * 7/1982 | Pomerantz | ................... 123/694 |
| 5,255,554 A | 10/1993 | Mallebrein et al. | |
| 5,298,865 A | 3/1994 | Denz et al. | |
| 5,313,121 A | * 5/1994 | Cianci et al. | ................ 327/103 |
| 5,359,852 A | * 11/1994 | Curran et al. | .................. 60/274 |
| 5,901,691 A | * 5/1999 | Katoh | .......................... 123/688 |
| 2004/0100271 A1 | * 5/2004 | Ikeda | .......................... 324/514 |

* cited by examiner

*Primary Examiner*—Charles Garber
(74) *Attorney, Agent, or Firm*—Denso Corporation

(57) ABSTRACT

An oxygen sensor abnormality detecting device has first and second offset circuits for applying first and second offset voltages to a ground line and an output line of an oxygen sensor. The device compares the voltage of the output line with a high voltage-side shorting determination value, a low voltage-side shorting determination value and a break determination value to detect a high voltage-side shorting, a low voltage-side shorting and a line break.

14 Claims, 10 Drawing Sheets

OXYGEN SENSOR ABNORMALITY DETECTING DEVICE HAVING OFFSET VOLTAGE CIRCUIT

CROSS REFERENCE TO RELATED APPLICATION

This application relates to and incorporates herein by reference Japanese Patent Application No. 2002-293738 filed on Oct. 7, 2002.

FIELD OF THE INVENTION

The present invention relates to an abnormality detecting device for detecting an abnormality of an oxygen sensor that detects the concentration of oxygen in the exhaust gas discharged from, for example, an engine of a vehicle.

BACKGROUND OF THE INVENTION

In order to clean the exhaust gas discharged from an engine of a vehicle, a catalyst unit such as a three-way catalyst is used. Further the supply state of fuel and air is controlled according to the concentration of oxygen in the exhaust gas.

In order to detect the concentration of oxygen in the exhaust gas, an oxygen senor ($O_2$ sensor), for example, a lambda sensor of the Nernst type is used. This sensor generates an electromotive force according to the concentration of oxygen.

This kind of oxygen sensor suffers from a disadvantage where an abnormality such as a shorting developed at the oxygen sensor might hinder the oxygen sensor from detecting the concentration of oxygen. Thus, U.S. Pat. No. 5,298,865 teaches a technology for detecting an abnormality of the oxygen sensor.

In this technology, as shown in FIG. 12, elements such as a pull-down resistor P4, an input resistor P5, and a capacitor P6 are connected to an output line P3 extending from an oxygen sensor P1 to an ADC (A/D converter) P2 connected to a microcomputer MC, and an offset voltage circuit P8 is connected to a ground line P7 to apply an offset voltage to the oxygen sensor P1.

As shown in FIG. 13A, in the case where the output voltage Vout of the oxygen sensor P1 is decreased below the offset voltage Voff during the operation of the oxygen sensor P1, it is determined that a low voltage-side shorting (ground shorting) is developed. In the case where the output voltage Vout is increased excessively above a usual range (1 V+Voff) of a sensor output, it is determined that a high voltage-side shorting is developed.

However, for example, in either case where a break or a low voltage-side shorting occurs in the output line P3 from which the output of the oxygen sensor P1 is taken out, the output voltage Vout of the oxygen sensor P1 is made lower than the offset voltage thereby to be brought to 0 volt. It is impossible to discriminate between the break and the low voltage-side shorting.

SUMMARY OF THE INVENTION

It is therefore an object of the invention to provide an oxygen sensor abnormality detecting device that can make a distinction between a break and a low voltage-side shorting in the oxygen sensor and accurately detect an abnormality of an oxygen sensor.

According to the invention, there is provided an oxygen sensor abnormality detecting device that detects an abnormality of the oxygen sensor connected to a ground line and an output line on the basis of a voltage applied thereto via the output line. In particular, an offset voltage circuit is provided for applying an offset voltage to the output line of the oxygen sensor via a predetermined resistor. This offset voltage is set to be outside an output range of the oxygen sensor under the normal operation. Preferably, another offset voltage circuit may be provided for applying another offset voltage to the ground line. The offset voltage circuits connected to the ground line and the output line operate as the first and the second offset circuits for applying the first and second offset voltages to the ground line and the output line, respectively.

In this manner, in the case when a low voltage-side shorting is developed in the output line, the output voltage of the oxygen sensor (that is, voltage applied to an abnormality detecting device side, for example, a microcomputer side: applied voltage) is brought to 0 V, so that it is possible to detect the occurrence of the low voltage-side shorting in the output line from this voltage.

On the other hand, in the case where a break occurs in the output line, voltage is not supplied by the oxygen sensor. However, the second offset voltage is applied to the output line (at a portion nearer to the abnormality detecting device than the broken point) via a resistor. In the case where a break occurs, the second offset voltage is applied to the abnormality detecting device. This second offset voltage is set at a value different from the output range during the normal operation of the oxygen sensor. When the second offset voltage is detected, it is possible to determine that a break occurs.

In this manner, a voltage applied to the abnormality detecting device (for example, ADC of the microcomputer) when the break occurs is different from a voltage applied thereto when the low voltage-side shorting is developed. Thus, based on the voltage applied to the abnormality detecting device, it is possible to accurately determine whether the break occurs or the low voltage-side shorting is developed.

In addition, In the case the second offset voltage is set at a value different from an output voltage range during the normal operation of the oxygen sensor, it is possible to detect the break with higher accuracy without confusing the second offset voltage with the normal output voltage of the oxygen sensor.

In this regard, the first offset voltage is applied to the ground line, so that the first offset voltage is added to the output voltage during the normal operation of the oxygen sensor. Then, as a matter of course, the first offset voltage is set at a value different from the second offset voltage so as to make a distinction between them.

Further, the first offset voltage is set at a value higher than the output voltage range of the oxygen sensor.

In this manner, in the case where the low voltage-side shorting is developed in the ground line, the output voltage of the oxygen sensor varies at values lower than the first offset voltage so that the low voltage-side shorting in the ground line can also be detected. Thus, it is possible to prevent a malfunction from being caused, for example, in an engine control responsive to the output of the oxygen sensor.

The resistor is a pull-down resistor having a large resistance. The use of this pull-down resistor reduces the influence of variations in the voltage when the oxygen sensor is active and hence the second offset voltage can be set only by the resistors, which leads to simplify the construction.

The resistance of the pull-down resistor is set according to an internal resistance when the oxygen sensor is inactive. As shown in FIG. 13B, in the related art, however large the resistance of the pull-down resistor may be, when the oxygen sensor is inactive (temperature is extremely low), the output voltage of the oxygen sensor is inevitably brought to a voltage lower than the offset voltage, which leads to detecting a failure by mistake and hence needs to set a determination prohibition time. However, the invention can shorten the determination prohibition time or eliminate the need for setting the determination prohibition time.

That is, for example, by selectively setting the resistance of the pull-down resistor at a value higher than the internal resistance of the oxygen sensor when the oxygen sensor is inactive to prevent the output voltage of the oxygen sensor from being applied to a break detection voltage, it is possible to eliminate the determination prohibition time (failure determination prohibition time) at the time immediately after the start of operation. For example, in the case where the internal resistance is 1 MΩ, the resistance of the pull-down resistor can be selectively set at a resistance of 1 MΩ or larger. Here, among the other methods, the selection of the pull-down resistance according to the internal resistance can also shorten the failure determination prohibition time.

If the second offset voltage is set at a value lower than the first offset voltage, in the case where such a low second offset voltage is detected, it is possible to determine that a break occurs.

If the second offset voltage is set at a value higher than a low voltage-side shorting determination value, that is, the second offset voltage is set at a value between the first offset voltage and the low voltage-side shorting determination value, in the case where the second offset value is detected, it is possible to accurately detect the occurrence of the break without determining by mistake that the low voltage-side shorting is developed.

If the second offset voltage is set at a value higher than an output range during the normal operation of the oxygen sensor, in the case where the second offset voltage higher than the output range, it is possible to determine that a break occurs. Here, in the case where the second offset voltage is set at a value higher than the first offset voltage, it is possible to set the second offset voltage on the basis of the first offset voltage. For example, the first offset voltage and the power supply voltage are split by resistors to set the second offset voltage).

If the second offset voltage is set at a value lower than a high voltage-side shorting determination value, that is, the second offset voltage is set at a value between the upper limit of the output range during the normal operation of the oxygen sensor and the high voltage-side shorting determination value, in the case where such a second offset voltage is detected, it is possible to accurately detect the occurrence of a break without determining by mistake that the high voltage-side shorting is developed.

If the first offset voltage and/or the second offset voltage are/is set by the use of resistors, for example, by reducing a power supply voltage of 5 V by the use of resistors, it is possible to easily provide the first offset voltage and the second offset voltage each having a desired voltage.

If the first offset voltage is outputted via an operational amplifier, it is possible to reduce the influence of variations in the voltage when the oxygen sensor is active and hence to provide the stable first offset voltage. Here, as for the second offset voltage, for example, by connecting a pull-down resistor having a large resistance, it is possible to stabilize the voltage and hence to omit an operational amplifier.

If the output voltage of the oxygen sensor and the first offset voltage are applied to a processing unit (for example, microcomputer) for detecting the abnormality of the oxygen sensor, it is possible to obtain a more correct net output voltage by the difference between both of the voltages. Thus, it is possible to detect the abnormality of the oxygen sensor with high accuracy. Then, it is also possible to detect the concentration of oxygen with high accuracy. Further, the use of the difference between the output voltage of the oxygen sensor and the first offset voltage eliminates the need for providing a unit (for example, an operational amplifier) for stabilizing the first offset voltage and hence produces an advantage of simplifying the construction. Still further, there is produced an effect that even if the low voltage-side shorting is developed in the ground line, a usual operation (measuring the concentration of oxygen) can be performed by the input state of both of the voltages.

If an abnormality detection is always performed not only after the oxygen sensor is increased to a usual operating temperature (when the oxygen sensor is active) but also immediately after the power supply is turned on before the oxygen sensor becomes active, it is possible to quickly detect the occurrences of a break and shorting. That is, it is possible to detect abnormalities in an instant irrespective of the operating conditions. This eliminates performing a control (for example, an air-fuel ratio control) by mistake on the basis of information relating to the erroneous output voltage of the oxygen sensor and hence can effectively clean the exhaust gas. Here, by storing the results of detection of the abnormalities as diagnostic data in a memory such as a nonvolatile memory and the like, it is possible to read and use them at the time of maintenance to be later performed. Moreover, it is possible to immediately announce the results of detection of the abnormalities by the use of alarming means such an alarm lamp and the like.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

First Embodiment

Figure 1:
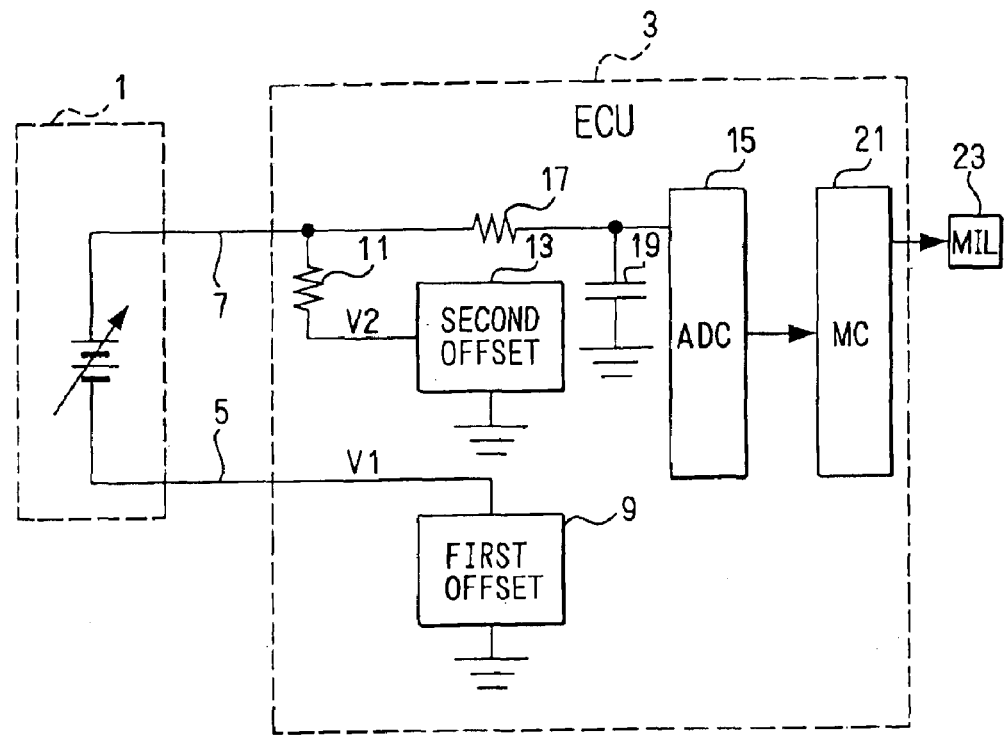
FIG. 1 is an illustration showing an oxygen sensor abnormality detecting device in a first embodiment of the present invention.

As shown in FIG. 1, an oxygen sensor ($O_2$ sensor) 1 used in the first embodiment is a lambda ($\lambda$) sensor of the Nernst type. This sensor 1 is fixed, for example, to an exhaust pipe, and its electromotive force (thus, output voltage) varies in response to the concentration of oxygen in the exhaust gas.

The oxygen sensor 1 is connected to an electronic control unit (ECU) 3 for measuring an oxygen concentration via a ground line 5 and an output line 7. This ECU 3 functions as an abnormality detecting device for detecting an abnormality of the oxygen sensor 1.

A first offset voltage circuit 9 for applying a first offset voltage V1 is connected to the ground line 5. On the other hand, a second offset voltage circuit 13 for applying a second offset voltage V2 is connected to the output line 7 via a pull-down resistor 11 (for example, 1.5 M$\Omega$). Further, an input resistor 17 (for example, 10 K$\Omega$) and an input capacitor 19 (for example, 0.1 $\mu$F) are connected to the output line 7 so as to make a voltage applied to an ADC (A/D converter) 15 a suitable value.

Here, as for the pull-down resistor 11, a resistor is selected which has a resistance beyond an internal resistance when the oxygen sensor 1 is inactive (temperature is extremely low).

Further, a microcomputer 21 that has a digital signal inputted from the ADC 15 and performs operation processing for detecting the abnormality of the oxygen sensor 1 is connected to the ADC 15. Here, a nonvolatile memory (for example, EEPROM) for storing the detection results of abnormalities and a lamp (for example, multifunction indicator lamp: MIL) 23 for alarming the detection results of abnormalities are connected to this microcomputer 21.

Figure 2:
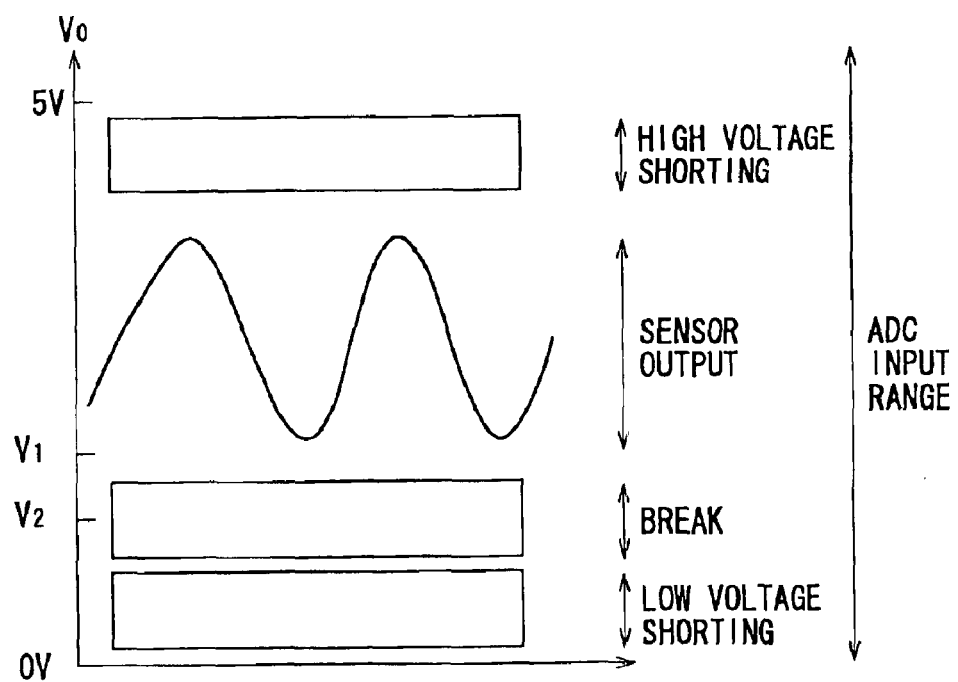
FIG. 2 is an illustration showing a principle of detecting an abnormality of the oxygen sensor in the first embodiment.

In particular, in the present embodiment, as shown in FIG. 2, the second offset voltage V2 is set at a lower value than the first offset voltage V1. Further, the detection range of the low voltage-side shorting is set at a lower range than that of the second offset voltage V2 (more specifically, detection range of a line break). Still further, the detection range of the high voltage-side shorting is set at a higher range than a range obtained by adding the first offset voltage V1 to the range of an output voltage when the oxygen sensor 1 normally operates, that is, a variation range (about 1 V) of net output of the oxygen sensor 1.

Figure 3:
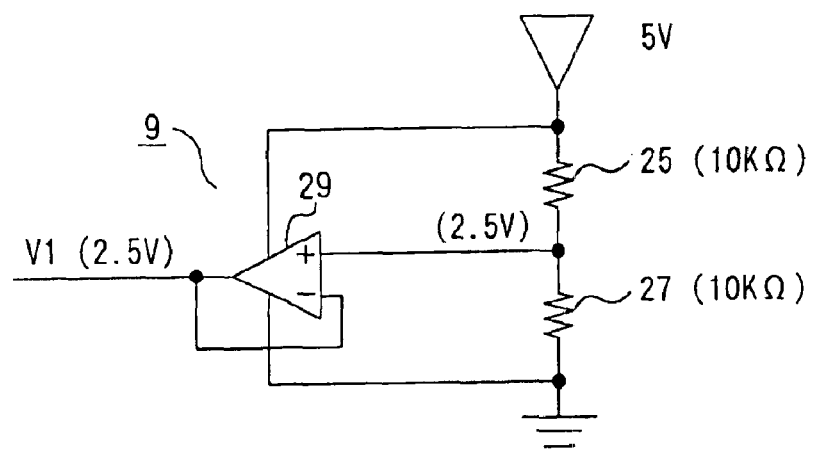
FIG. 3 is a circuit diagram showing a first offset voltage circuit in the first embodiment.

Moreover, as shown in FIG. 3, the first offset voltage circuit 9 is a combination of a first resistor 25 and a second resistor 27 each of which has the same resistance, and an operational amplifier 29. That is, a power source voltage of 5 V, for example, is applied to the first resistor 25 (10 K$\Omega$) and the second resistor 27 (10 K$\Omega$) and thereby a voltage (2.5 V) taken out of the middle point of both resistors 25 and 27 is applied to the operational amplifier 29. Thus, the stable first offset voltage (having little variations in voltage) of the same 2.5 V can be supplied by the operational amplifier 29.

Figure 4A:
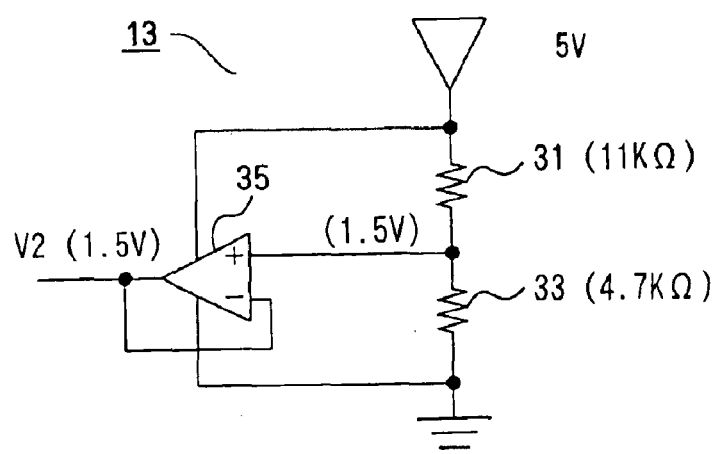
FIG. 4A is a circuit diagram showing a second offset voltage circuit in the first embodiment.

On the other hand, as shown in FIG. 4A, the second offset voltage circuit 13 is a combination of a first resistor 31 and a second resistor 33 each of which has a different resistance, and an operational amplifier 35. That is, a power source voltage of 5 V, for example, is applied to the first resistor 31 (11 K$\Omega$) and the second resistor 33 (4.7 K$\Omega$) and a voltage (1.5 V) obtained at the middle point of both resistors 31, 33 is applied to the operational amplifier 35. Thus, the stable second offset voltage V2 of the same 1.5 V can be supplied by the operational amplifier 35.

Figure 4B:
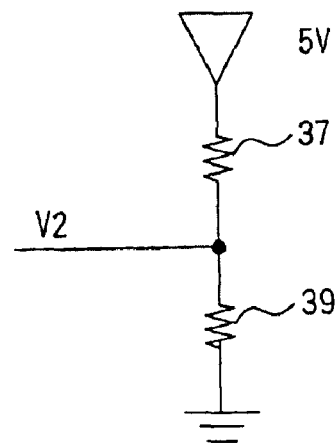
FIG. 4B is a circuit diagram showing another second offset voltage circuit.

In this regard, in the present embodiment, the pull-down resistor 11 having a large resistance is connected to the second offset voltage circuit 13 thereby to reduce the effect of variations in voltage. Thus, as shown in FIG. 4B, it is also recommended that the second offset voltage V2 be developed by the use of only the first resistor 37 and the second resistor 39.

When the oxygen sensor 1 normally operates, as shown in FIG. 2, a variation range of the output voltage Vo is about 1 V. However, In the case the first offset voltage V1 of 2.5 V is applied to the ground line 5 by the first offset voltage circuit 9, the actual output voltage of the oxygen sensor 1 (that is, voltage applied to the ECU 3) varies in a higher range than the output voltage in the case where the first offset voltage V1 is not applied. For example, the actual output voltage of the oxygen sensor 1 Varies within a range of about 1 V, for example, from 2.5 V to 3.5 V.

Therefore, the ECU 3 converts this output voltage Vo into a digital signal by the ADC 15 and inputs the digital signal to the microcomputer 21. The microcomputer 21 finds a actual (net) output voltage by subtracting the offset voltage (fixed value) from this output voltage. This actual output voltage corresponds to the concentration of oxygen and hence the concentration of oxygen can be found from the actual output voltage, for example, by the use of a data map.

Figure 5A:
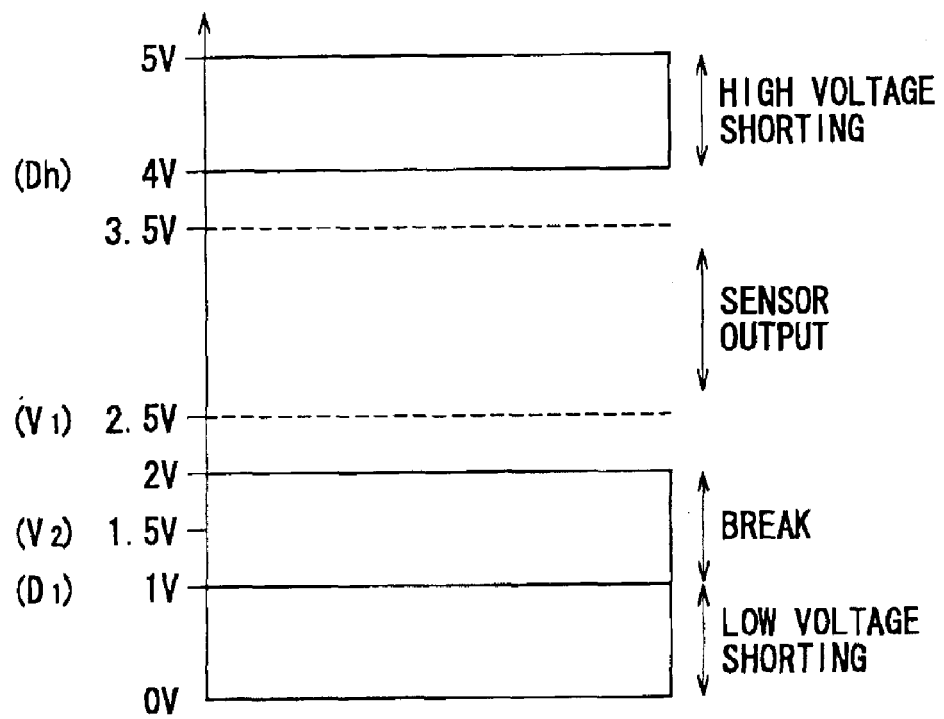
FIG. 5A is an illustration showing determination values in the detection of an abnormality of the oxygen sensor in the first embodiment.

In the present embodiment, as shown in FIG. 5A, determination values are set for determining abnormalities of a break, a low voltage-side shorting, and a high voltage-side shorting, respectively.

Specifically, a low voltage-side shorting determination value Dl for determining a low voltage-side shorting is set at 1 V. In the case where the output voltage of the oxygen sensor 1 is lower than the lower voltage-side shorting determination value Dl, it is determined that the low voltage-side shorting is developed.

That is, in the case where the low voltage-side shorting is developed in the output line 7, the output voltage of the oxygen sensor 1 is brought to a low voltage of 0 V. Thus, in the case where the output voltage is brought to a value lower than 1 V of the low voltage-side shorting determination value Dl, it is determined that the low voltage-side shorting is developed.

Further, In the case the second offset voltage V2 is 1.5 V, in the case where the output voltage of the oxygen sensor 1 ranges from 1.0 V to 2.0 V across the second offset voltage V2, that is, from 1.0 V which is the low voltage-side shorting determination value to 2.0 V which is a determination value for making a distinction between the first offset voltage V1 and the second offset voltage V2, it is determined that a line break occurs.

That is, in the case where a break of line occurs in the output line 7, the output voltage of the oxygen sensor 1 is not applied to the ADC 15 but the second offset voltage is applied to the ADC 15 and is detected by the microcomputer 21. Thus, in the case where a voltage ranging from 1.0 V to 2.0 V (including 1.5 V) is detected, it is determined that the line break occurs.

Further, the high voltage-side shorting determination value Dh for determining the high voltage-side shorting is set at 4.0 V (above the output voltage when the oxygen sensor 1 normally operates). In the case where the output voltage of the oxygen sensor 1 is above the high voltage-side shorting determination value Dh, it is determined that the high voltage-side shorting is developed.

That is, in the case where the high voltage-side shorting is developed in the output line 7, the high voltage is applied to the output line 7 and hence the microcomputer 21 detects a high voltage near 5 V as an output voltage. Thus, in the case where the output voltage is increased to a value higher than 4 V of the high voltage-side shorting determination value Dh, it is determined that the high voltage-side shorting is developed.

In this regard, when an abnormality is detected, the first offset voltage V1 which is a fixed value is subtracted from the voltage applied to the ADC 15 to find the net output voltage of the oxygen sensor 1 and the concentration of oxygen and the abnormality of the oxygen sensor 1 can be detected based on this net output voltage. For the sake of simplicity, however, descriptions will be made by the use of the voltage applied to the ADC 15 (voltage including the first offset voltage at the normal operation).

Figure 6:
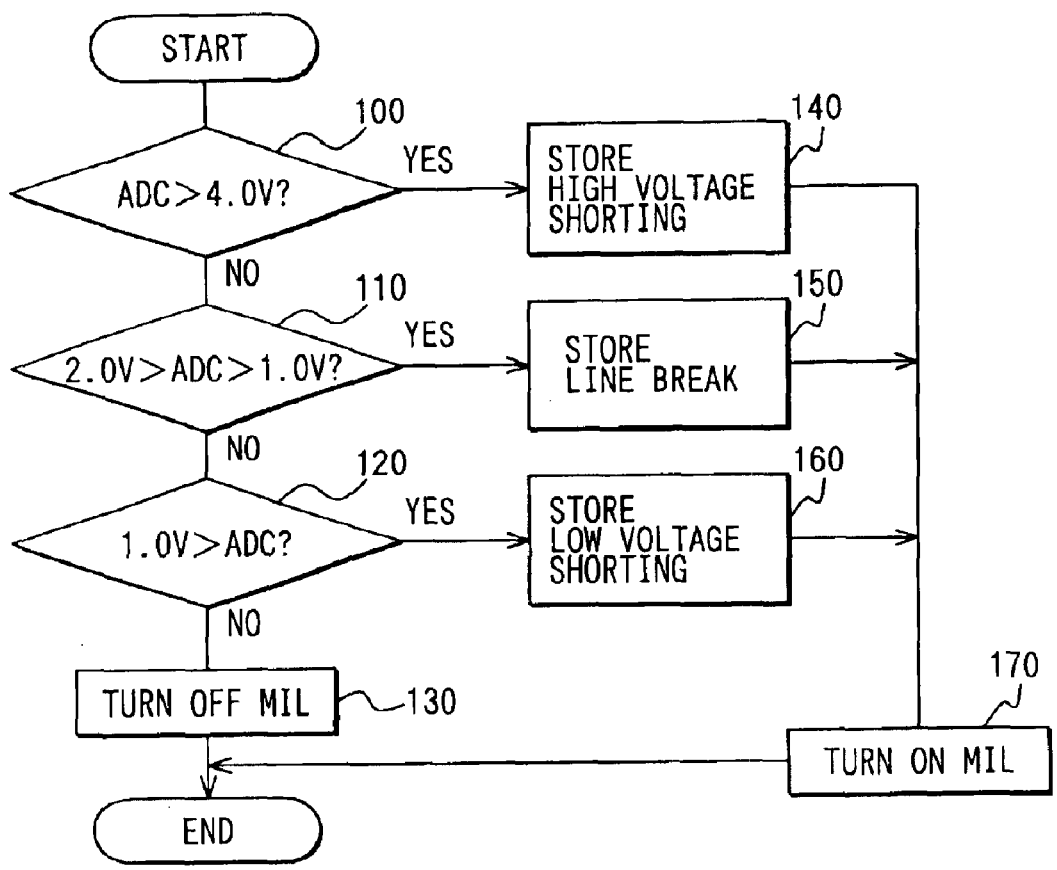
FIG. 6 is a flow chart showing processing of detecting an abnormality of the oxygen sensor in the first embodiment.

The microcomputer 21 is programmed perform the processing of FIG. 6 to detect an abnormality of the oxygen sensor 1. This processing is performed immediately and at regular time intervals after a power to the oxygen sensor 1 is turned on (an ignition switch is turned on) by the microcomputer 21.

In this processing, it is determined at step 100 whether or not the voltage applied to the ADC 15 is higher than 4.0 V of the high voltage-side shorting determination value Dh. If the determination result is YES, the processing advances to step 140, whereas if the determination result is NO, the processing advances to step 110.

In the case the applied voltage is higher than the high voltage-side shorting determination value Dh, it is determined at step 140 that high voltage-side shorting is developed and a diagnostic code of the high voltage-side shorting is stored in a nonvolatile memory.

At the following step 170, in order to announce the occurrence of an abnormality, a request of lighting a MIL (malfunction indicator light) is outputted thereby to light the MIL 23 and then the present processing is once finished.

On the other hand, it is determined at step 110 whether or not the applied voltage is within a range of from 2.0 V which is a determination value of the offset voltage difference (which makes a distinction between the first offset voltage and the second offset voltage) to 1.0 V which is the low voltage determination value Dl. Here, if the determination result is YES, the processing advances to step 150, whereas if the determination result is NO, the processing advances to step 120.

Since it is determined that a break occurs in the output line 7, a diagnostic code of a break is stored in the nonvolatile memory at step 150. Then the processing advances to step 170 where the processing of lighting the MIL 23 is performed in the same way and then the present processing is once finished.

On the other hand, it is determined at step 120 whether or not the applied voltage is lower than 1.0 V which is the low voltage-side shorting determination value Dl. Here, if the determination result is YES, the processing advances to step 160. If the determination result is NO, the processing advances to step 130.

In the case the applied voltage is lower than the low voltage-side shorting determination value Dl, it is determined that the low voltage-side shorting is developed and a diagnostic code of the low voltage-side shorting is stored in the nonvolatile memory at step 160. The processing advances to step 170 where the processing of lighting the MIL 23 is performed in the same way and then the present processing is once finished.

By the above processing, the occurrences of the high voltage-side shorting, the break, and the low voltage-side shorting are detected. The diagnostic codes of the detection results are stored and the MIL 23 is lighted thereby to inform the abnormality of the oxygen sensor 1.

According to the first embodiment, the first offset voltage V1 is applied to the ground line 5 and the second offset voltage V2 is applied to the output line 7 via the pull-down resistor 11 and the processing of detecting abnormalities shown in FIG. 6 is performed. Thus, it is possible to accurately determine the occurrences of the high voltage-side shorting, the line break, and the low voltage-side shorting, respectively.

Of the above occurrences, at the occurrences of the break and the low voltage-side shorting, the voltage is not brought to 0 V as in the related art device, but is brought to different voltages, so it is possible to clearly discriminate between the break and the low voltage-side shorting. Additionally, particularly when the break occurs, the second offset voltage V2 different from the output range when the oxygen sensor 1 normally operates is applied to the ADC 15. It is possible to make an accurate determination of the break irrespective of the operating condition of the oxygen sensor 1.

Further, In the case the detection result of the abnormality is stored as the diagnostic data, it is possible to easily repair the oxygen sensor 1, and In the case the detection result of the abnormality is informed by the MIL 23, a driver can immediately notice the occurrence of the abnormality.

Still further, in the present embodiment, the operational amplifier 29 is used in the first offset voltage circuit 9. It is therefore possible to reduce the effect of variations in voltage when the oxygen sensor 1 is active and to stabilize the first offset voltage.

In addition, In the case the operational amplifier 35 is used also in the second offset voltage circuit 13, the second offset voltage can similarly be stabilized.

Figure 5B:
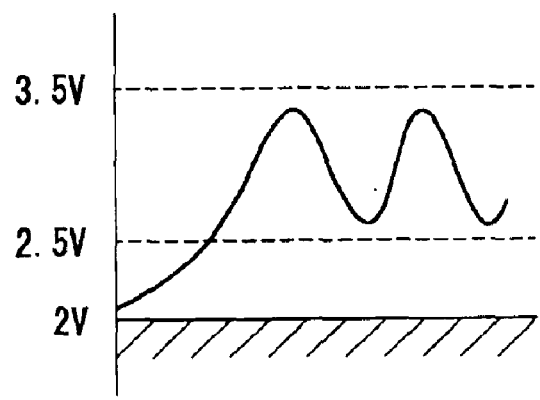
FIG. 5B is an illustration showing a sensor output immediately after the start of operation.

Still further, in the present embodiment, a pull-down resistance higher than the internal resistance when the oxygen sensor 1 is inactive is selected to prevent the output of the oxygen sensor 1 from being applied to a break detection voltage, so that it is possible to eliminate a failure determination prohibition time at the start of operation and hence to start a failure determination immediately from a start of supplying power to the sensor as shown in FIG. 5B.

Still further, in the present embodiment, the first offset voltage is set at a value higher than the output voltage of the oxygen sensor 1, so that it is possible to detect also the low voltage-side shorting of the ground line 5 and hence to prevent a malfunction from being caused.

Here, In the case the pull-down resistor 11 having a large resistance is connected to the second offset voltage circuit 13, the second offset voltage circuit 13 is little affected by variations in voltage and hence the operational amplifier 35 can be omitted. In this case, it is possible to set the voltage only by the resistors and hence to simplify the construction of the second offset voltage circuit 13.

Second Embodiment

Figure 7A:
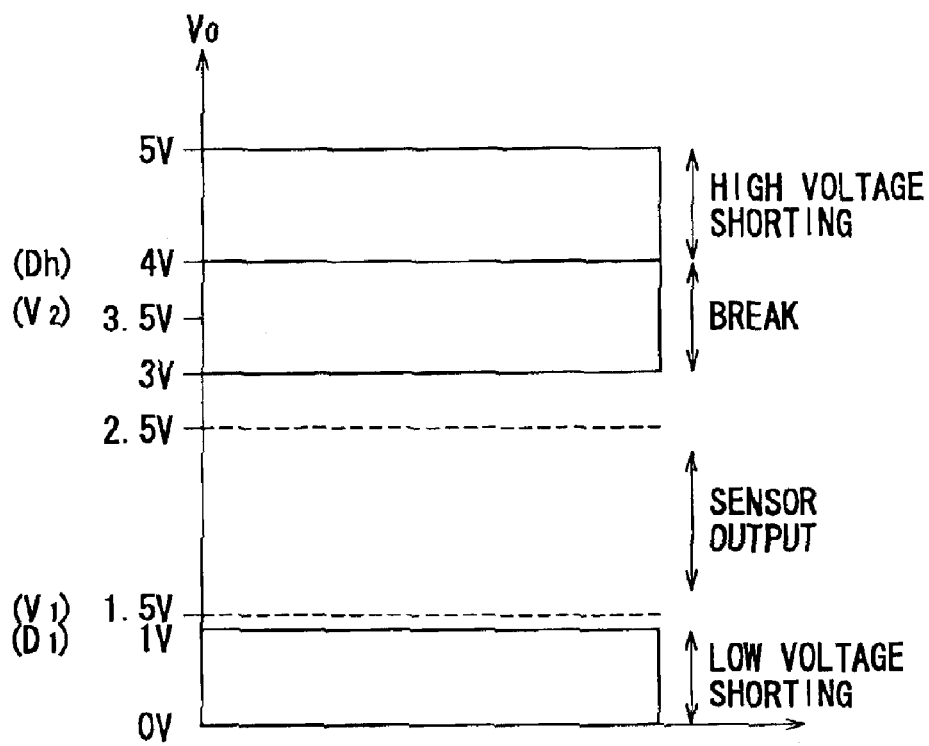
FIG. 7A is an illustration showing determination values in the detection of an abnormality of the oxygen sensor in a second embodiment of the present invention.

In the second embodiment, as shown in FIG. 7A, the first offset voltage V1 is set at 1.5 V and the second offset voltage V2 is set at 3.5 V. That is, the second offset voltage V2 is set at a higher value than the output voltage (about 1.5 V to 2.5 V) of the oxygen sensor 1 to which the first offset voltage V1 is added.

Further, the first offset voltage circuit 9 for supplying the first offset voltage has the nearly same construction as in the first embodiment, but the resistances of the resistors for supplying the respective voltages are different from those in the first embodiment.

Specifically, in order to provide the first offset voltage V1 of 1.5 V, a resistor of 11 KΩ is used as the first resistor 25 of the first offset voltage circuit 9 and a resistor of 4.7 KΩ is used as the second resistor 27. Moreover, in order to provide the second offset voltage V2 of 3.5 V, a resistor of 4.7 KΩ is used as the first resistor 31 of the second offset voltage circuit 13 and a resistor of 11 KΩ is used as the second resistor 33.

Further, as shown in FIG. 7A, determination values Dl and Dh are set to determine the respective abnormality determinations.

Specifically, the low voltage-side shorting determination value Dl for determining the low voltage-side shorting is set at 1.0 V which is lower than the first offset voltage V1 of 1.5 V. In the case where the output voltage of the oxygen sensor 1 is lower than the low voltage-side shorting determination value Dl, it is determined that the low voltage-side shorting is developed.

Then, the high voltage-side shorting determination value Dh for determining the high voltage-side shorting is set at 4.0 V which is higher than the second offset voltage V2 of 3.5 V. In the case where the output voltage of the oxygen sensor is higher than the high voltage-side shorting determination value Dh, it is determined that the high voltage-side shorting is developed.

Further, the output voltage (varying within a range of about 1.0 V) of the oxygen sensor 1 to which the first offset voltage V1 is added is lower than 3 V. In the case where the output voltage of the oxygen sensor 1 is within a range of from 3.0 V (which is the upper limit of the output voltage) to 4.0 V (which is the high voltage-side shorting determination value Dh), it is determined that a break occurs.

That is, in the second embodiment, the second offset voltage V2 is not set at a value lower than the first offset voltage as is the case with the first embodiment, but is set at a value higher than the output voltage of the oxygen sensor 1. Thus, in the case where a break occurs, the second offset voltage V2 of about 3.5 V is applied to the ADC 15. Thus, in the case where the second offset voltage V2 higher than the output voltage of the oxygen sensor 1 is detected, it is possible to determine that a break occurs.

Figure 8:
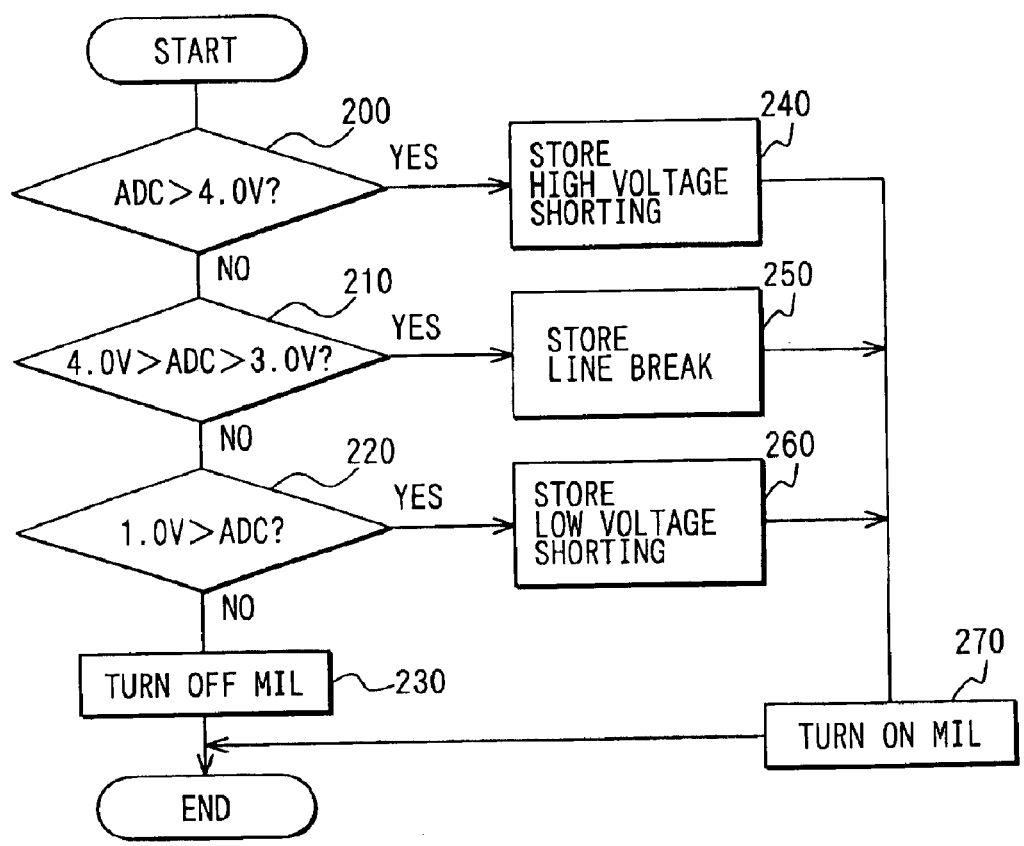
FIG. 8 is a flow chart showing processing of detecting an abnormality of the oxygen sensor in the second embodiment.

In the second embodiment, as shown in FIG. 8, it is determined at step 200 whether or not the voltage applied to the ADC 15 is higher than 4.0 V which is the high voltage-side shorting determination value Dh. If the determination result is YES, the processing advances to step 240. If the determination result is NO, the processing advances to step 210.

In the case the applied voltage is higher than the high voltage-side shorting determination value Dh, it is deter-mined that the high voltage-side shorting is developed, and a diagnostic code of the high voltage-side shorting is stored in the nonvolatile memory at step 240.

At the following step 270, in order to announce the occurrence of the abnormality, a MIL lighting request is outputted to light the MIL 23 and then the present processing is once finished.

On the other hand, at step 210, it is determined whether or not the applied voltage is a value within a range of from 4.0 V to 3.0 V, which shows the occurrence of a line break. If the determination result is YES, the processing advances to step 250. If the determination result is NO, the processing advances to step 220.

In the case it is determined that a break occurs in the output line 7, a diagnostic code of the break is stored in the nonvolatile memory at step 250. Then, the processing advances to step 270 where processing of lighting the MIL 23 is performed in the same way.

On the other hand, it is determined at step 220 whether or not the applied voltage is lower than 1.0 V which is the low voltage-side shorting determination value Dl. Here, if the determination result is YES, the processing advances to step 260. If the determination result is NO, the processing advances to step 230.

In the case the applied voltage is lower than the low voltage-side shorting and hence it is determined that the low voltage-side shorting is developed, a diagnostic code of the low voltage-side shorting is stored in the nonvolatile memory at step 260. Then, the processing advances to step 270 where the processing of lighting the MIL 23 is similarly performed.

By the above processing, the occurrences of the high voltage-side shorting, the break, and the low voltage-side shorting are detected and the diagnostic codes of the detection results are stored. Further, MIL 23 is lighted thereby to inform the abnormalities.

The second embodiment is different from the first embodiment with respect to the first offset voltage and the second offset voltage. However, in the second embodiment, as is the case with the first embodiment, the first offset voltage V1 is applied to the ground line 5 and the second offset voltage V2 is applied to the output line 7 via the pull-down resistor 11 so that the abnormality detection processing shown in FIG. 8 is performed. Thus, it is possible to accurately determine the high voltage-side shorting, the break, and the low voltage-side shorting.

Figure 7B:
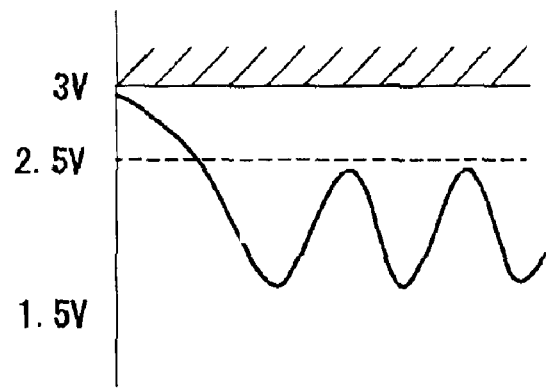
FIG. 7B is an illustration showing a sensor output immediately after the start of operation.

Moreover, as shown in FIG. 7B, also in the present embodiment, by selecting the pull-down resistance higher than the internal resistance when the oxygen sensor is inactive, the output of the oxygen sensor 1 is not applied to a break detection voltage. Thus, it is possible to eliminate a failure determination prohibition time at the start of the operation.

Third Embodiment

Figure 9:
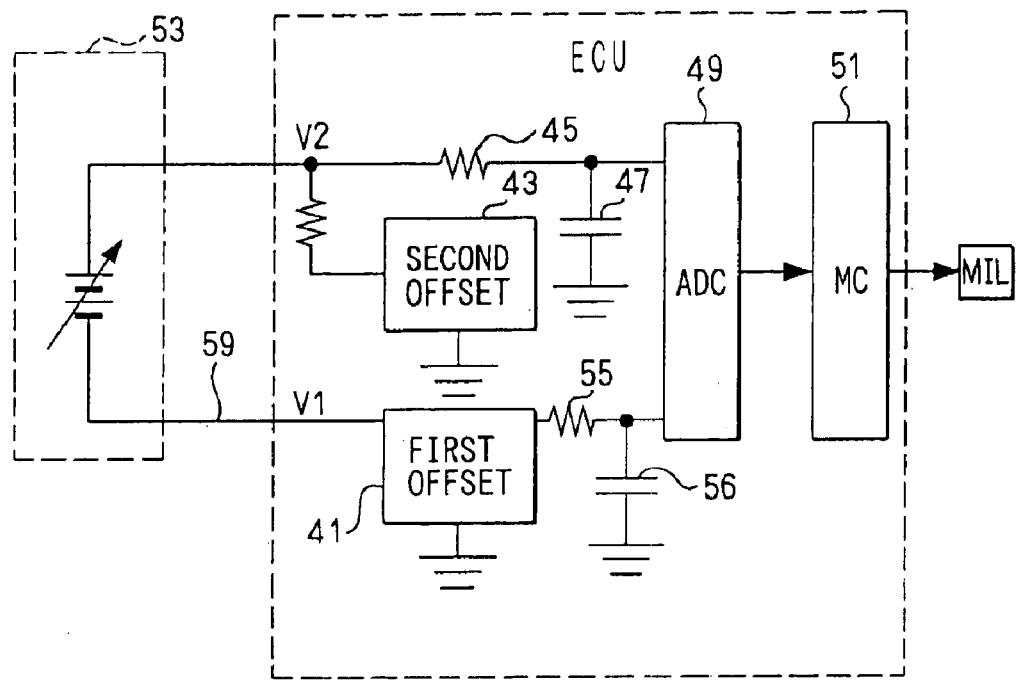
FIG. 9 is an illustration showing a an oxygen sensor abnormality detecting device in a third embodiment of the present invention.

As shown in FIG. 9, in the third embodiment, as is the case with the first and the second embodiments, there are provided a first offset voltage circuit 41, a second offset voltage circuit 43, an input resistor 45, an input capacitor 47, an ADC 49 and a microcomputer 51. The first offset voltage V1 is applied to the ADC 49 via a circuit to which an input resistor 55 and an input capacitor 56 are connected.

When the microcomputer 51 performs the processing of detecting an abnormality, the first offset voltage V1 of a fixed value is not subtracted from the output voltage of an oxygen sensor 53, but an actual first offset voltage, which is directly applied to the ADC 49 via the different input resistor 55, is subtracted from the output voltage of the oxygen sensor 53 to find the net output voltage of the oxygen sensor 53 and the processing of determining an abnormality is performed based on this output voltage.

In this manner, in the third embodiment, the same effects produced in the second and the third embodiments can be produced and the influence of variations in the first offset voltage V1 can be eliminated. Thus, the present embodiment has an advantage of detecting an abnormality and the concentration of oxygen with higher accuracy.

Further, the third embodiment can produce an advantage that, even if a low voltage-side shorting is developed in the ground line 59, a usual operation of measuring the concentration of oxygen can be performed from the input state of both voltages.

Figure 10:
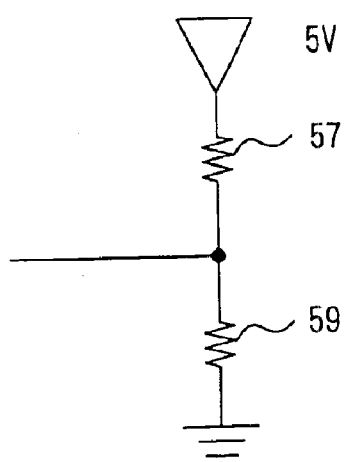
FIG. 10 is a circuit diagram of a first offset voltage circuit and a second offset voltage circuit in the third embodiment.

Still further, in the present embodiment, the influence of variations in the first offset voltage can be eliminated and hence an operational amplifier for stabilizing the first offset voltage V1 is not required. Thus, for example, as shown in FIG. 10, in the first offset voltage circuit 41 and the second offset voltage circuit 43, the first offset voltage and the second offset voltage can be set by a resistance dividing method using a first resistor 57 and a second resistor 59.

Here, the resistances of the respective resistors 57 and 59 are the same as those in the first embodiment.

Fourth Embodiment

Figure 11A:
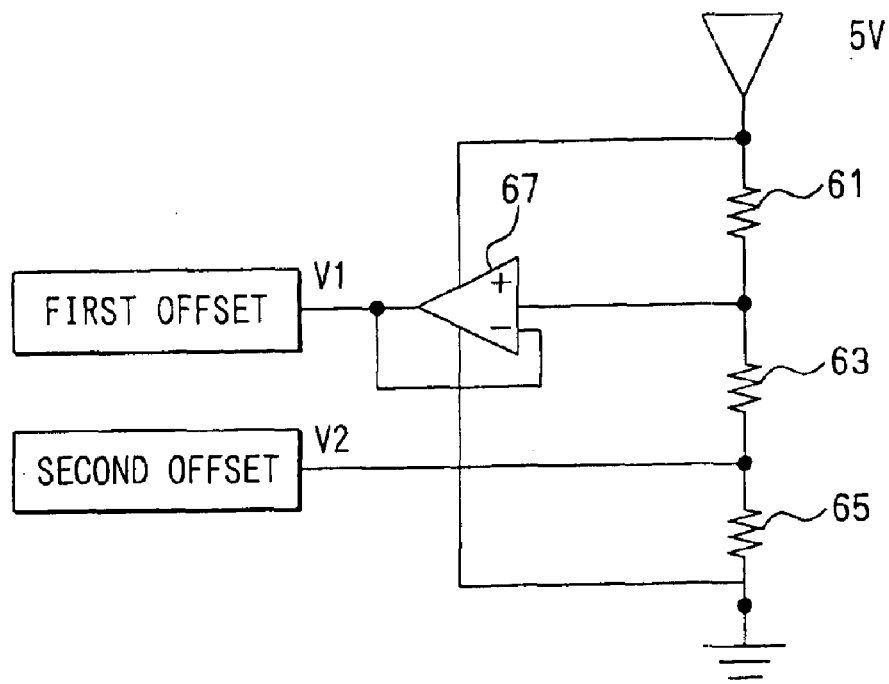
FIG. 11A is a circuit diagram of an offset voltage circuit in a fourth embodiment of the present invention.

In the fourth embodiment, as shown in FIG. 11A, the first offset voltage V1 and the second offset voltage V2 are set by the use of the same voltage circuit.

That is, a first resistor 61 (11 KΩ), a second resistor 63 (4.7 KΩ) and a third resistor 65 (6.2 KΩ) are connected in series to a voltage circuit for applying a power source voltage of 5 V, and the first offset voltage V1 (2.5 V) is taken out between the first resistor 61 and the second resistor 63 via an operational amplifier 67.

Further, the second offset voltage V2 (1.5 V) can be taken out between the second resistor 63 and the third resistor 65.

Also in this case, there is produced the same effect as in the first embodiment, and the use of only three resistors 61, 62 and 63 can provide an advantage of making the construction simple.

Figure 11B:
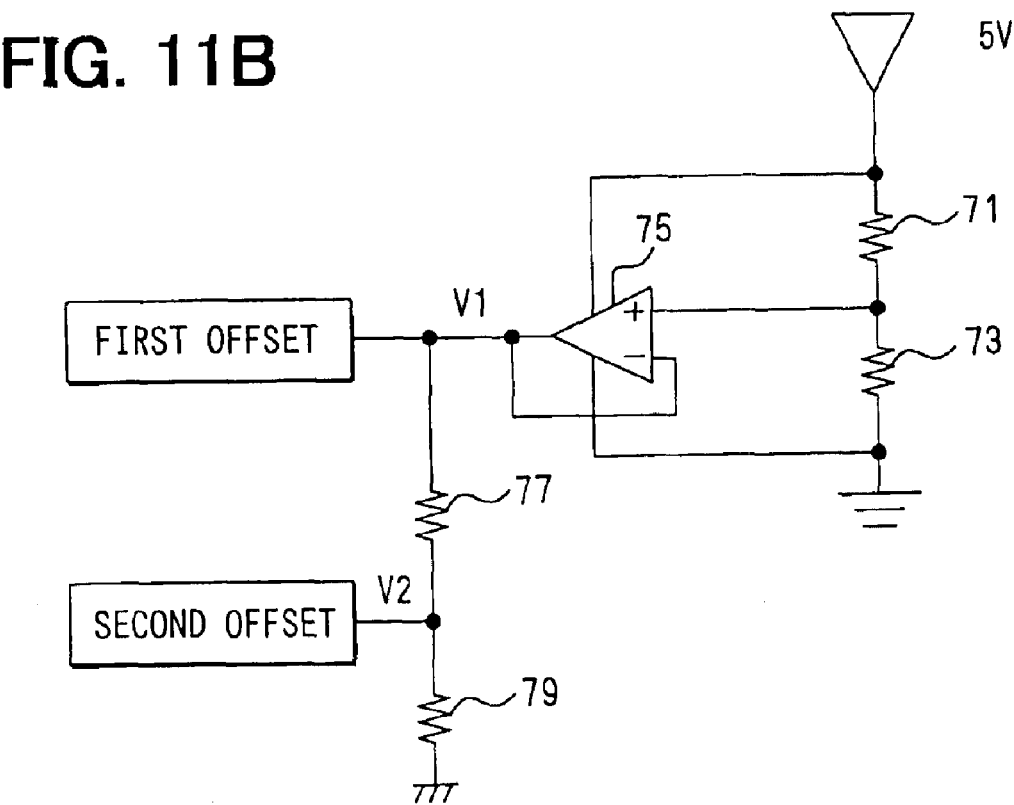
FIG. 11B is a circuit diagram of another offset voltage circuit.
Figure 12:
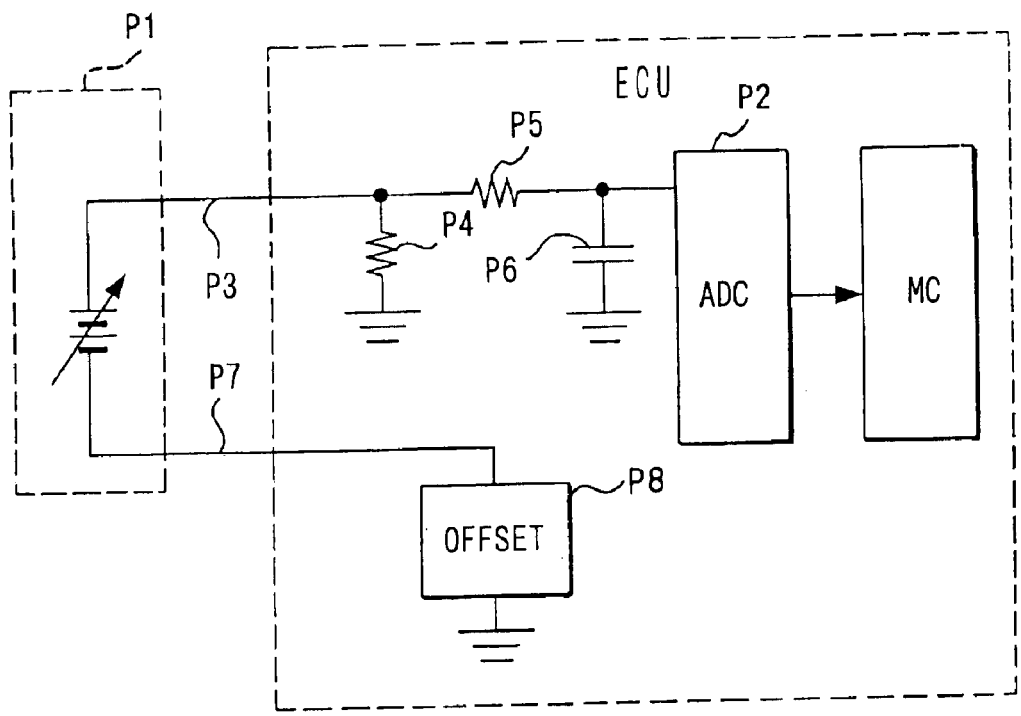
FIG. 12 is an illustration showing an oxygen sensor abnormality detecting device in a related art.
Figure 13A:
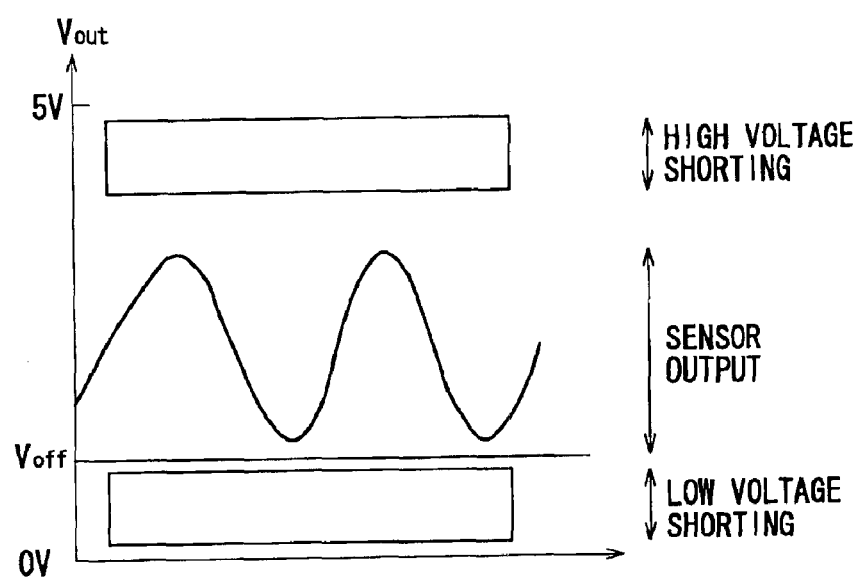
FIG. 13A is an illustration showing determination values in the detection of an abnormality of the oxygen sensor in the related art.
Figure 13B:
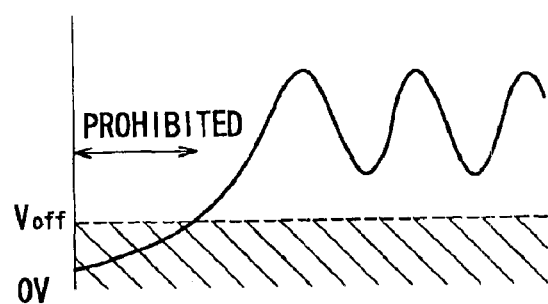
FIG. 13B is an illustration showing a sensor output immediately after the start of operation.

Still further, as shown in FIG. 11B, a first resistor 71 (10 KΩ) and a second resistor 73 (10 KΩ) are connected in series to a voltage circuit for applying a power source voltage of 5 V and the first offset voltage V1 (2.5 V) is taken out between the first resistor 71 and the second resistor 73 via an operational amplifier 75.

Still further, a third resistor 77 (4.7 KΩ) and a fourth resistor 79 (6.2 KΩ) are connected in series between the first offset voltage V1 and the ground, so that the second offset voltage (1.5 V) is taken out between the third resistor 77 and the fourth resistor 79.

Also, in this case, there is produced the same effect as in the first embodiment.

The present invention is not limited to the above disclosed embodiments but may be put into practice in other embodiments without departing from the spirit of the invention.

What is claimed is:

1. An oxygen sensor abnormality detecting device, the device being connectable to the oxygen sensor through a ground line and an output line for detecting an abnormality of the oxygen sensor on the basis of a voltage applied thereto via the output line, the device comprising:

first offset voltage applying means for applying a first offset voltage to the ground line; and second offset voltage applying means for applying a second offset voltage to the output line via a resistor, the second offset voltage being set to be outside a normal output range of the oxygen sensor.

2. The abnormality detecting device as in claim 1, wherein the first offset voltage is set to be higher than the normal output voltage range of the oxygen sensor.

3. The abnormality detecting device as in claim 1, wherein the predetermined resistor is a pull-down resistor.

4. The abnormality detecting device as in claim 3, wherein a resistance of the pull-down resistor is set to be higher than an internal resistance of the oxygen sensor under an inactive condition.

5. The abnormality detecting device as in claim 1, wherein the second offset voltage is set to be lower than the first offset voltage.

6. The abnormality detecting device as in claim 5, wherein the second offset voltage is set to be higher than a low voltage-side shorting determination value for determining a low voltage-side shorting.

7. The abnormality detecting device as in claim 1, wherein the second offset voltage is set to be higher than an output voltage range of the oxygen sensor under a normal operation condition.

8. The abnormality detecting as in claim 7, wherein the second offset voltage is set to be lower than a high voltage-side shorting determination value for determining a high voltage-side shorting.

9. The abnormality detecting device as in claim 1, wherein at least one of the first offset voltage and the second offset voltage is set by voltage dividing resistors.

10. The abnormality detecting device as in claim 1, wherein the first offset voltage is outputted via an operational amplifier.

11. The abnormality detecting device as in claim 1, further comprising:

a processing unit for receiving an output voltage of the oxygen sensor and the first offset voltage and detecting an abnormality of the oxygen sensor based on a difference between the output voltage and the first offset voltage.

12. The abnormality detecting device as in claim 1, further comprising:

a processing unit for performing an oxygen sensor abnormality detection operation immediately after a start of an oxygen concentration detecting operation of the oxygen sensor.

13. The abnormality detecting device as in claim 1, further comprising:

an A/D converter connected to the output line for converting a voltage signal inputted via the output line into a digital signal; and a microcomputer for detecting an abnormality of the oxygen sensor by comparing the digital signal outputted by the A/D converter with two different shorting determination values and a break determination value.

14. The abnormality detecting device as in claim 1, further comprising:

an A/D converter for directly receiving a voltage signal outputted by the oxygen sensor and converting the inputted voltage signal into a digital signal; and a microcomputer for detecting an abnormality of the oxygen sensor based on the digital signal outputted by the A/D converter.

* * * * *